(12) United States Patent
Casso

(10) Patent No.: US 6,685,693 B1
(45) Date of Patent: Feb. 3, 2004

(54) METHOD OF PREPARING A SYRINGE FOR INJECTION

(76) Inventor: J. Michael Casso, 700 Ave. A, Westwego, LA (US) 70094

( * ) Notice: Subject to any disclaimer, the term of this patent is extended or adjusted under 35 U.S.C. 154(b) by 390 days.

(21) Appl. No.: 09/634,284

(22) Filed: Aug. 9, 2000

(51) Int. Cl.$^7$ .............................................. A61M 31/00
(52) U.S. Cl. ..................................... 604/500; 366/267
(58) Field of Search ............................ 604/500, 82–88, 604/181, 187, 188, 191; 222/1, 52, 54, 56, 71, 147, 160, 163, 145.5, 145.6, 137; 366/130, 267, 269; D24/108, 112, 130

(56) References Cited

U.S. PATENT DOCUMENTS

| | | | |
|---|---|---|---|
| 3,010,705 A | * 11/1961 | Brown | ........................ 366/268 |
| 3,662,517 A | 5/1972 | Tascher et al. | |
| 3,734,147 A | 5/1973 | Borutta et al. | |
| 3,770,026 A | 11/1973 | Isenberg | |
| 3,807,467 A | 4/1974 | Tascher et al. | |
| 3,907,009 A | 9/1975 | Dobbins | |
| 3,993,063 A | 11/1976 | Larrabee | |
| 4,196,732 A | 4/1980 | Wardlaw | |
| 4,219,055 A | 8/1980 | Wright | |
| 4,501,306 A | 2/1985 | Chu et al. | |
| 4,581,015 A | * 4/1986 | Alfano | ........................ 604/88 |
| 4,940,460 A | 7/1990 | Casey et al. | |
| 5,292,318 A | 3/1994 | Haber et al. | |
| 5,330,430 A | 7/1994 | Sullivan | |
| 5,425,580 A | * 6/1995 | Beller | ........................ 366/131 |
| 5,584,814 A | 12/1996 | Schuster et al. | |
| 5,620,422 A | 4/1997 | Halbich | |
| 5,647,409 A | 7/1997 | Christ et al. | |
| 5,704,921 A | 1/1998 | Carilli | |
| 5,716,345 A | 2/1998 | Halbich | |
| 5,746,733 A | 5/1998 | Capaccio et al. | |
| 5,755,696 A | 5/1998 | Caizza | |
| 5,807,374 A | 9/1998 | Caizza et al. | |
| 5,832,971 A | 11/1998 | Yale et al. | |
| 5,842,326 A | 12/1998 | Wolf | |
| 5,865,227 A | 2/1999 | Carilli | |
| 5,887,633 A | 3/1999 | Yale et al. | |
| 5,911,252 A | * 6/1999 | Cassel | ........................ 141/234 |
| 5,928,215 A | 7/1999 | Caizza et al. | |

FOREIGN PATENT DOCUMENTS

EP 0 734 708 A1 10/1996

* cited by examiner

*Primary Examiner*—LoAn H. Thanh
(74) *Attorney, Agent, or Firm*—Kilpatrick Stockton LLP

(57) ABSTRACT

The present invention provides simple manual methods of filing a syringe, wherein the wastage of liquid is reduced, and the need to replace a damaged delivery needle is avoided. The methods of the present in invention comprise the filling of a distributing syringe with a liquid from a supply vial, placing the distributing syringe in communication with at least one receiving syringe, and transferring the liquid to the receiving syringe whereon the receiving syringe is filled. Communication between the distributing syringe and the receiving syringe is preferably achieved by inserting the hypodermic needle of the distributing syringe into the nozzle of the receiving syringe. A multiplicity of syringes may be filled from one distributing syringe by repeating the steps of needle insertion and liquid transfer. A delivery needle is attached to each receiving syringe, which is then used to administer the liquid to an animal or human. A single distributing syringe avoids the use of a fresh supply vial for the charging of each receiving syringe, lessening the losses of excess volumes of the liquid that remain in the supply vials.

10 Claims, 2 Drawing Sheets

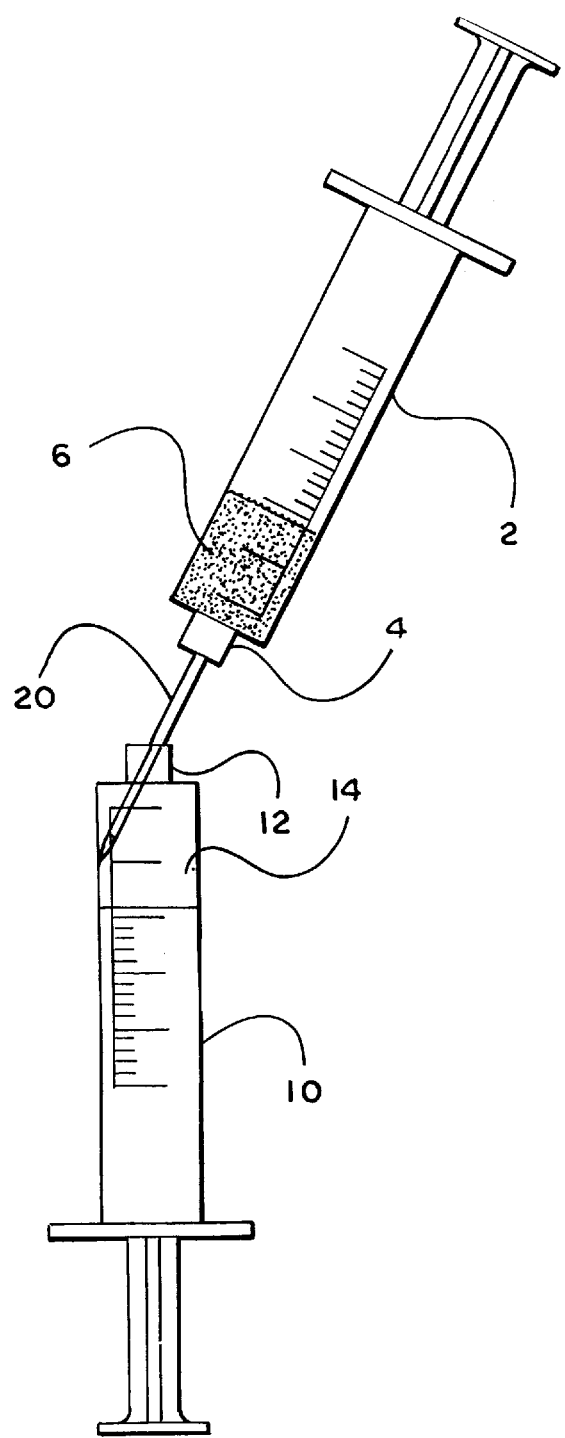
Fig_1

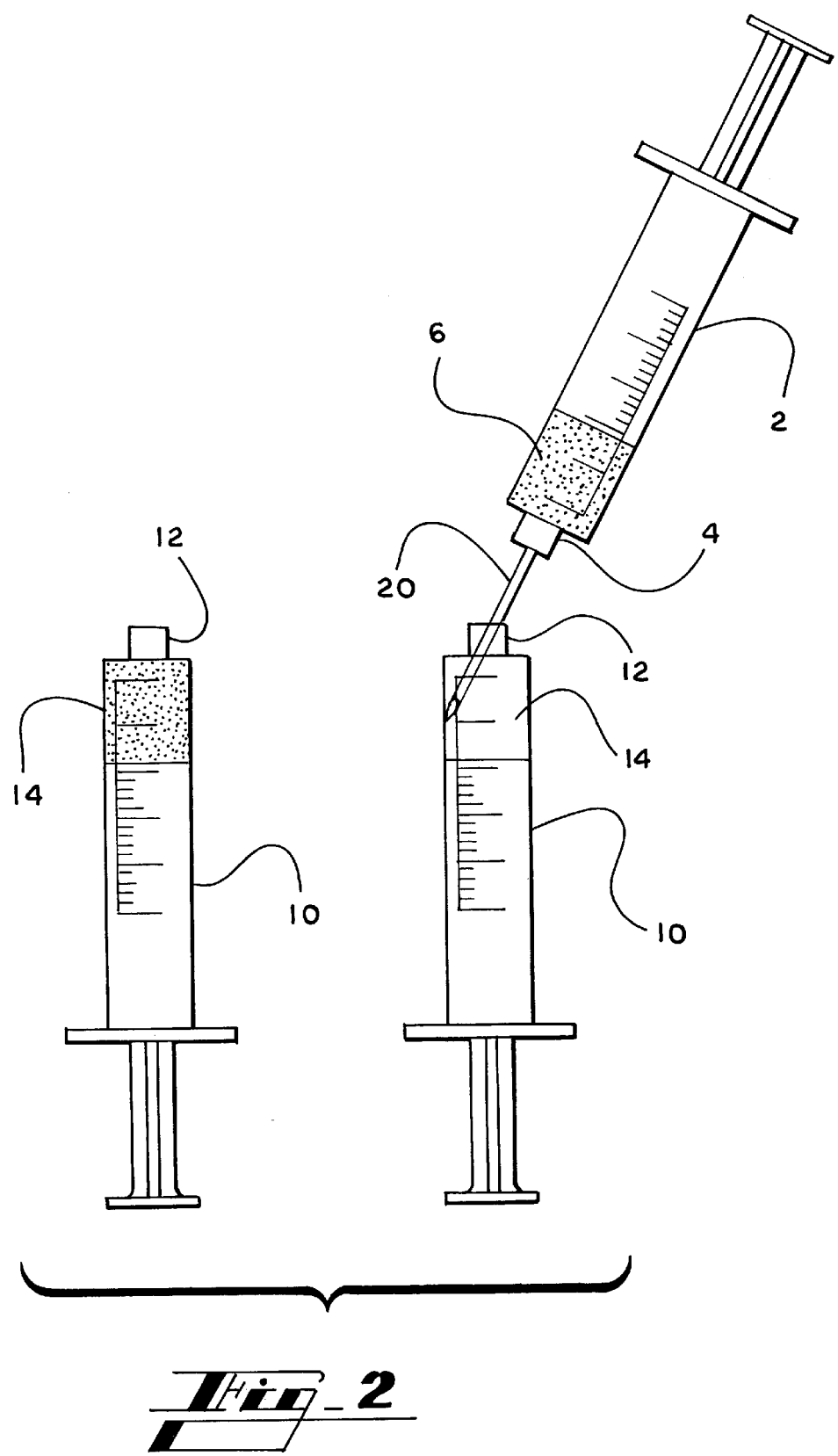
Fig_2

METHOD OF PREPARING A SYRINGE FOR INJECTION

FIELD OF THE INVENTION

The present invention relates to methods of filling a syringe that reduce wastage of a liquid used to fill the syringe, and of damaged hypodermic needles.

BACKGROUND

Medical hypodermic syringes are typically filled by attaching a hypodermic needle to the body of a syringe, penetrating a sealing septum of a medicinal liquid supply vial and withdrawing the liquid stored therein into the body of the syringe. Alternatively, the liquid to be loaded is supplied in a glass vial, and the heat-sealed neck is removed before inserting the needle of the syringe to extract the liquid.

The charging or loading process, however, often results in wastage of some of the liquid. This occurs most frequently when a residual volume remains in the supply vial from which the liquid has been extracted. The excess liquid that remains in the vial after extraction of the selected pharmaceutical dose is included by both practical necessity and mandated by regulation of pharmaceutical products. It serves to ensure that the full amount of the prescribed dose of a medication is received into the syringe and thereby administered to a patient.

A second source of waste of liquid during the standard method of filling a syringe arises out of the common technique of eliminating air both from the body of a liquid-charged syringe and the lumen of the attached hypodermic needle. This particular step in the process cannot be avoided, as to do so would introduce the risk of injecting air into the blood stream and creating an air embolism, with potentially fatal consequences. The method that is commonly adopted, therefore, is to slightly depress the plunger of the syringe to eject small volume of liquid, simultaneously forcing out any entrapped air. To ensure that all gas bubbles are dislodged from the interior walls of the syringe barrel, the syringe is sharply tapped, an action that may also dislodge a volume of liquid from the needle tip.

While small in themselves, the accumulated losses of liquid may become quite considerable. When the liquid is a pharmaceutical preparation, the economic loss of a drug may be significant. The possibility of accidental contamination of the syringe user, a bystander or the patient by dislodged liquid from the needle tip is another potentially dangerous consequence of the syringe filling technique most commonly practiced.

A further disadvantage of the standard manual procedure for charging a medical hypodermic syringe is that frequently a small gauge needle is required for the subsequent inoculation into an animal or human. Many liquid pharmaceutical products however are supplied in vials sealed by a flexible septum. It is intended that penetrating this septum with a hypodermic needle and withdrawing the liquid from the vial into body of the syringe will charge the syringe. The thickness and density of the sealing septum of a liquid supply vial can easily result in the bending or blunting of a piercing hypodermic needle. This, of course, renders it useless for the subsequent penetration into the skin of the recipient individual. Since a replacement needle may be necessary, needle costs will double and become an additional burden on medical facilities already under financial constraint.

Several apparatus of varying degrees of complexity have been devised that will charge a multiplicity of syringes, or the automatic charging of a single syringe. None of these devices, however, overcomes the need to further dislodge any introduced gas bubbles. These devices, therefore, still result in some losses of the liquid.

What is needed, therefore, are methods of filling syringes that avoid the wastage of the liquid that can occur during the filling procedure itself. There is also a need to avoid the necessity of replacing the hypodermic syringe needle that was used in the process of charging the syringe with a liquid, with a fresh needle immediately prior to transdermal injection of the liquid. What is also needed is a method of charging multiple syringes from a single liquid supply vial so that there is no repetitive wastage of the liquid when each syringe is filled, and so that there is a single penetration of the sealing septum of the liquid supply vial. What is also required is a simple manual method of charging multiple syringes with a reduced likelihood of entrapping gas bubbles.

SUMMARY OF THE INVENTION

The present invention solves the problems described above by providing simple manual methods of filling a syringe, wherein the wastage of liquid is reduced, and the need to replace a damaged delivery needle is avoided.

Charging a syringe with a liquid from a supply vial leaves behind a residual unusable, and therefore wasted, volume of the liquid in the supply vial. Further loss of liquid occurs when eliminating entrapped air from within the syringe and the attached needle. Wastage also occurs if a hypodermic needle becomes deformed or otherwise damaged during the piercing of the sealing septum of a liquid supply vial.

The methods of the present invention therefore comprise the filling of a distributing syringe with a liquid from a supply vial, placing the distributing syringe in communication with at least one receiving syringe, and transferring the liquid to the receiving syringe whereupon the receiving syringe is filled. Communication between the distributing syringe and the receiving syringe is preferably achieved by inserting the hypodermic needle of the distributing syringe into the nozzle of the receiving syringe. A multiplicity of syringes may be filled from one distributing syringe by repeating the steps of needle insertion and liquid transfer. Depressing the plunger of the delivery system and filling the receiving syringe to a predetermined volume eliminates entrapped air within the receiving syringes. A delivery needle is attached to the receiving syringe, which is then used to administer the liquid to an animal or human.

The method of the present invention allows the charging of multiple receiving syringes from a single distributing syringe without the necessity of reloading the distributing syringe.

The method of the present invention avoids the use of a fresh supply vial for the charging of each receiving syringe, thereby lessening the losses of excess volumes of the liquid that remain in the supply vials.

The method of the present invention also limits the penetration of a sealing septum of a supply vial to the needle attached to the distributing syringe. Accordingly, it is an object of the present invention to provide a method of filling a syringe whereby wastage of a liquid is minimized and replacement needles are avoided.

It is an object of the present invention to provide a method of loading a distributing syringe with a liquid, filling at least one receiving syringe with liquid transferred from the distributing syringe so that wastage of a residual liquid in a supply vial is minimized.

It also is an object the present invention to provide a method of filling at least one receiving syringe without damaging and wasting small gauge hypodermic needles by penetration through a sealing septum of a liquid supply vial.

It yet another object of the present invention to provide a manual method of filling at least one receiving syringe from a distributing syringe so as to avoid residual gas bubbles in the receiving syringe.

These and other features, objects and advantages of the in invention and preferred embodiments of the present invention will become apparent from the detailed description that follows.

BRIEF DESCRIPTION OF THE DRAWINGS

FIG. 1 is a drawing of the present invention.

FIG. 2 is a drawing of the present invention with additional receiving syringe.

DETAILED DESCRIPTION OF THE INVENTION

The present invention provides methods of filling a syringe wherein residual, unused volumes of medicinal liquid from a supply vial are reduced in scale, and wastage of the liquid is minimized. This is accomplished by means of a distributing syringe capable of being charged from a supply vial with a volume of liquid. The liquid, or a portion thereof, can than be transferred to a multiplicity of receiving syringes in such a manner that undesirable gas bubbles are not introduced into the bodies of the receiving syringes. The methods of the present invention also avoid damage to hypodermic needles by reducing their use in penetrating the sealing septum of a liquid supply vial, and by allowing the use of a gauge of hypodermic needle that resists damage during the piercing of the septum. Therefore, the first use of the needle of a receiving syringe is in a human or animal and, since the sharp needle has not been blunted or otherwise damaged, there is reduced resistance to skin penetration with less pain and discomfort to the recipient.

The present invention offers the advantage over existing procedures for the filling of a syringe that multiple receiving syringes may be charged from a single distributing syringe, thereby reducing wastage of any residual liquid remaining in the supply vial. Multiple receiving syringes may be filled from a single distributing syringe, charged from one supply vial.

The present invention offers the further advantage that the delivery syringe may be charged from a liquid supply vial by means of a large gauge hypodermic needle that resists damage caused by penetration of the sealing septum of the liquid supply vial. After the liquid is transferred to a receiving syringe, a narrow gauge needle may be attached to the receiving syringe for administration of the liquid to a patient. The narrow gauge needle, therefore, does not encounter the resistant sealing septum, and therefore is not blunted or otherwise damaged before piercing the skin of the recipient animal or human.

The present invention therefore offers a simple manual method of filling a syringe that significantly reduces wastage of a liquid. The present invention offers a means of filling multiple syringes with minimal liquid loss, and avoids damage to the syringe needle before inoculation that would otherwise require needle replacement.

Definitions:

The terms "supply vial" or "liquid supply vial" refer to any container from which a liquid to be administered to an animal or human by means of a hypodermic syringe is supplied. The vial may be, but is not limited to, a vessel sealed with a septum, a vial sealed by a heat-created seal of the container wall, or any other container with a liquid known to one skilled in the art.

The term "septum" refers to a flexible or rigid membrane that can be pierced by a hypodermic needle and which is used to seal an opening to a container. The septum can be made of rubber, plastic, a plastic polymer or any other suitable material known to one of ordinary skill in the art.

The term "syringe" refers to a device comprising a hollow body and a moveable plunger, forming a variable volume region therein. At one end of the barrel is a male connector "nozzle" for fitting into a female connection "hub 4" with a hypodermic single lumen needle.

The term "distributing syringe" refers to a syringe used to withdraw liquid from a supply vial for dispensing to a multiplicity of receiving syringes.

The term "receiving syringe" refers to a syringe capable of accepting liquid from a delivery syringe, and which may then be used to administer the liquid to an animal or human.

The terms "liquid" or "fluid" refer to any liquid or fluid to be administered to an animal or human. These terms refer to, but are not limited to, medicinal solutions or liquid compositions of pharmaceutical preparations, vaccines, drugs, medications, or of any other substances of therapeutic, biochemical or genetic activity.

The term "gauge" refers to the diameter of a hypodermic single lumen needle.

The term "hypodermic syringe needle" refers to any cannulated needle and having a hub or other means of attachment to the nozzle of the syringe. The end of the needle opposed to the syringe may be, but is not limited to, a sharpened end to more readily penetrate skin.

The terms "loading", "filling" or "charging" refer to a process whereby a syringe receives a liquid into the variable volume region.

Method of the Present Invention

The methods of filling syringes provided herein are intended to charge at least one receiving syringe in such a way that there is minimal wastage of the liquid loaded and administered to an animal or human. This is achieved in the present invention by interposing a distributing, or delivery, syringe between a supply vial and a multiplicity of receiving syringes that ultimately are used to administer the liquid to an animal or human. Thus there is achieved withdrawal of a fluid from a single supply vial. The only residual volume that then remains, and is ultimately lost, is in the one supply vial, even though the liquid may be dispensed to, and fill, a multiplicity of receiving syringes. The alternative, and traditional method, is to fill each receiving syringe directly from a fresh liquid vial, with the attendant wastage of the residual liquids in each vial.

The methods of the present invention do not use the distributing syringe to directly administer a liquid to an animal or human. A hypodermic needle attached to the distributing syringe, therefore, may be selected that has a gauge sufficient to resist damage when penetrating a sealing septum of a supply vial. The receiving syringe need only be fitted with a needle of narrow gauge for subsequent administration of the liquid to the animal or human.

The needle attached to the distributing syringe is between about 12 and about 30 gauge. A 20 gauge needle is preferred. The distributing syringe has a variable volume region with a volume in the range of about 3.0 cc to about 30.0 cc. The volume of liquid receivable by the receiving syringe is preferably in the range of about 1.0 cc to about 10.0 cc. The plunger of the receiving syringe can be withdrawn to adjust the variable volume region of the syringe to a volume that is greater than the volume of the predetermined dose of the liquid to be administered to an animal or human.

A preferred embodiment of the present invention is a method of filling a syringe, wherein a distributing syringe 2 is loaded with a liquid from a supply vial, placed in communication with a receiving syringe 10, and a predetermined volume of the liquid 6 is transferred from the distributing syringe to the receiving syringe.

A preferred embodiment of the present invention is a method of loading a syringe, comprising the steps of: (a) fitting a distributing syringe with a single lumen hypodermic needle 20 that can resist damage when piercing a septum, (b) loading the distributing syringe with a liquid, (c) removing gas bubbles from the liquid in the distributing syringe, (d) selecting at least one receiving syringe having a variable volume, a plunger, and a nozzle 12, (e) withdrawing the plunger of the receiving syringe, thereby adjusting the variable volume region to a predetermined volume 14, (f) placing the needle of the distributing syringe into the variable volume region of the receiving syringe through the nozzle of the receiving syringe, wherein the liquid in the distributing syringe can be transferred to the variable volume region of the receiving syringe, (g) transferring liquid from the distributing syringe to the variable volume region of the receiving syringe, (h) fitting the receiving syringe with a hypodermic needle, and (i) removing gas bubbles from the liquid in the variable volume region of the receiving syringe.

In a preferred embodiment, the tip of the hypodermic needle of the distributing syringe is placed inside and against the wall of the receiving syringe prior to transferring the liquid.

In a preferred embodiment of the present invention, the receiving syringe has a volume less than the volume of the liquid in the distributing syringe, and an attached needle of between 12 and 30 gauge.

In the most preferred embodiment of the present invention, the receiving syringe has an attached needle of between 16 and 27 gauge.

A preferred embodiment of the method of the present invention is where the adjusted variable volume of the receiving syringe is larger than the predetermined volume of the dose of the liquid to be administered to an animal or human.

Yet another preferred embodiment of the present invention is a method of loading a receiving syringe, wherein the adjusted variable volume of the receiving syringe is between about 0.01 cc and about 0.05 cc greater than the predetermined volume of the dose of the liquid to be administered to an animal or human.

It is advantageous to prepare at the same time multiple receiving syringes for fluid transfer. This can be achieved by withdrawing the plungers of each receiving syringe to a pre-selected volume as described, and standing each one on end with the nozzles facing upward, supported by a rack. Therefore, it is understood that all of the receiving syringes may be sequentially filled with fluid, and then all of the receiving syringes may be fitted with hypodermic needles.

It should be understood, of course, that the foregoing relates only to preferred embodiments of the present invention and that numerous modifications or alterations may be made therein without departing from the spirit or the scope of the invention. The invention will be described in greater detail by way of a specific example. The following example is offered for illustrative purposes, and is intended neither to limit nor define the invention in any manner.

EXAMPLE

A distributing syringe was fitted with a 20 gauge hypodermic single lumen needle capable of penetrating a sealing septum of a liquid supply vial. The maximum capacity of the syringe was 30 cc. The distributing syringe was selected so that the volume of the liquid loaded into the syringe from the supply vial exceeded that of an individual receiving syringe. The distributing syringe pierced the septum of the vial and 20 cc of liquid was withdrawn into the distributing syringe.

Six receiving syringes were selected, each with a maximum liquid capacity of 5 cc. The plungers of the receiving syringes were withdrawn so as to adjust the variable volume region of each syringe to the final selected volume of liquid to be administered to an animal or human, 3 cc. The plungers were then further withdrawn, to increase the available capacity of each receiving syringe by an additional 0.02 cc to compensate for liquid necessary to fill the hypodermic needle to be attached thereto.

The tip of the hypodermic needle of the distributing syringe was inserted through the nozzle and into the interior of, the receiving syringe so that the tip of the hypodermic needle touched the interior surface of the variable volume region of the receiving syringe to minimize the creation of air bubbles during transfer of the liquid. The plunger of the distributing syringe was slowly depressed, thereby transferring liquid from the distributing syringe to the interior variable volume region of the receiving syringe. Sufficient liquid was transferred to fill the available volume within the receiving syringe. Gas bubbles created within the interior of the receiving syringe were removed by back priming the distributing syringe.

The hypodermic needle attached to the distributing syringe was slowly withdrawn from the nozzle of the receiving syringe. The hub of a 27 gauge hypodermic needle was then attached to the nozzle of the receiving syringe. The body of the syringe was inverted and tapped to dislodge any remaining gas bubbles, and the plunger depressed so that the receiving syringe contained only the predetermined volume of the liquid to be administered as a dose to a recipient animal or human. The transfer of fluid was repeated with the five additional syringes.

We claim:

1. A method of preparing a syringe for injection, comprising the steps of:

(a) loading a distributing syringe with a liquid, (b) placing the distributing syringe in communication with a receiving syringe having a nozzle and a pre-selected volume region surrounded by walls, wherein the distributing syringe has a hypodermic needle attached thereto which is placed within the nozzle of the receiving syringe, (c) transferring a predetermined volume of the liquid from the distributing syringe to the pre-selected volume region of the receiving syringe, and (d) repeating the steps (b) and (c) with at least one additional syringe.

2. The method of loading a syringe as in claim 1, wherein the needle is between about 12 and abut 30 gauge.

3. The method of loading a syringe as in claim 1, wherein the needle is between 16 and 27 gauge.

4. The method of loading a syringe as in claim 1, wherein the distributing syringe has a variable volume region with a maximum volume in the range of about 3.0 cc to about 30.0 cc.

5. The method of loading a syringe as in claim 1, wherein the distributing syringe has a variable volume region with a maximum volume in the range of about 1.0 cc to about 10.0 cc.

6. The method of loading a syringe as in claim 1, wherein an adjusted variable volume region of the receiving syringe has a volume less than the volume of the liquid in the distributing syringe.

7. The method of loading a syringe as in claim 1, wherein the needle attached to the distributing syringe is placed against the wall of the receiving syringe.

8. The method of loading a syringe as in claim 1, wherein an adjusted variable volume region of the receiving syringe is larger than a predetermined volume equal to a dose of the liquid to be administered to an animal or human.

9. The method of loading a syringe as in claim 1, wherein an adjusted variable volume of the receiving syringe is between about 0.01 cc and about 0.05 cc greater than the predetermined volume.

10. The method of loading a syringe as in claim 1, further comprising a step of adjusting the variable volume region of the receiving syringe to the predetermined volume.

* * * * *